United States Patent [19]
Honeybourne

[11] Patent Number: 5,663,072
[45] Date of Patent: Sep. 2, 1997

[54] FOOD SPOILAGE DETECTION METHOD

[75] Inventor: Colin Lucas Honeybourne, Wotton-Under-Edge, England

[73] Assignee: British Technology Group Ltd, London, England

[21] Appl. No.: 256,095

[22] PCT Filed: Jan. 25, 1993

[86] PCT No.: PCT/GB93/00155

§ 371 Date: Jun. 24, 1994

§ 102(e) Date: Jun. 24, 1994

[87] PCT Pub. No.: WO93/15403

PCT Pub. Date: Aug. 5, 1993

[30] Foreign Application Priority Data

Jan. 24, 1992 [GB] United Kingdom .................. 9201568

[51] Int. Cl.$^6$ .......................... G01N 33/12; G01N 21/31
[52] U.S. Cl. ................... 436/20; 436/21; 436/128; 436/167; 436/169
[58] Field of Search ............... 436/20–24, 127, 436/128, 164, 168, 167, 169

[56] References Cited

U.S. PATENT DOCUMENTS 4,285,697  8/1981  Neary .
5,310,682  5/1994  Novotny et al. .................. 436/128

FOREIGN PATENT DOCUMENTS 2 013 336  8/1979  United Kingdom .

OTHER PUBLICATIONS

Ishida, J. et al. "4,5–Diaminophthalydrazide as a highly sensitive chemiluminescence derivatization reagent for a–dicarbonyl compounds in high–perfromance liquid chromatography" Journal of Chromatography, vol. 598 (1992) pp. 203–208.

Maroulis, A.J. "Flurometric Determination of Biacetyl" Talanta, vol. 32, No. 6 (1985) pp. 504–506.

DePablo, B. et al. "The D(–)lactic acid and acetoin/diacetyl as potential indicators of the microbial quality of vacuum––packed pork and meat products" Journal of Applied Bacteriology, vol. 66 (1989) pp. 185–190.

Pietro, D. et al. "Determination of diacetyl in butter as 2,3–diaminonaphthalene derivative, using a fluorometric procedure or reverse phase liquid chromatography with fluorescence detection" Chemical Abstracts, vol. 109 (1988) Abstract No. 91320n.

Iwaida, M. et al. "Studies on the determianation of the aroma compounds produced by Streptococcus diacetilactis" Chemical Abstracts, vol. 68 (1968) Abstract No. 67827x.

Iwaida, M. et al. "The diacetyl and ethanol contents of commercial venegars and composite products containing vinegar" Chemical Abstracts, vol. 93 (1980) Abstract No. 44135x.

G. Sadler et al. "Diacetyl measurement in orange juice . . . " Journal of Food Science, vol. 55 No. 4, 1990, pp. 1164–1165.

R. H. Dainty et al. "Time course of volatile compound . . . " Journal of Applied Bacteriology, vol. 59 No. 4, Oct. 1985, Oxford, GB, pp. 303–309.

R.H. Dainty et al. "Time course of volatile compound . . . " Journal of Applied Bacteriology, vol. 66 No. 4, Apr. 1990, Oxford, GB, pp. 281–289.

Chemical Abstracts, vol. 110 No. 13, 27 Mar. 1989, Columbus, Ohio US, #113300. Estepa et al. "Spectrophotometric determination . . . ", p. 565.

Chemical Abstracts, vol. 113 No. 21. 19 Nov. 1990, Columbus, Ohio US, #191592. Choo et al. "A new type of organocobalt complex . . . ", p. 747.

Chemical Abstracts, vol. 103 No. 15, 14 Oct. 1985, Columbus, OH US, #119176, Duenas et al. "Specific nuclear staining of leukocytes . . . ", p. 356.

Database WPI, Section Ch. Week 8038, 29 Oct. 1980, Derwent Publications Ltd., London, GB, Class G, p. 7.

Primary Examiner—Jeffrey Snay
Attorney, Agent, or Firm—Nixon & Vanderhye

[57] ABSTRACT

Diacetyl, especially resulting from spoilage of chilled red meat, is monitored by exposing an aromatic ortho-diamine at acidic pH to an environment containing, or possibly containing, diacetyl and detecting any change in absorption or reflection of electromagnetic radiation due to the ortho-diamine.

13 Claims, 2 Drawing Sheets

FOOD SPOILAGE DETECTION METHOD

This invention relates to a method of detecting food (including beverage) spoilage and is particularly, although not exclusively, concerned with the detection of spoilage in chilled foodstuffs, such as red meats, during processing, transportation and/or storage.

BACKGROUND OF THE INVENTION

The monitoring and control of the condition of fresh foodstuffs, which have been given enhanced, but not indefinite, shelf life by chilling and refrigerated storage, poses a major problem in our health conscious society. Thus the consumer demands fresh food, conveniently packaged, and with all-the-year round availability in shops and supermarkets, while at the same time insisting that there is no danger of spoilage leading to impaired looks or flavour, or, more importantly, health risk, in the purchased foods.

Oxidation of lipids, nucleotide degradation by endogenous enzymes and bacterial growth processes involving the metabolism of a wide range of food constituents including carbohydrates and amino acids can all contribute to losses in sensory qualities of foods and their ultimate rejection by the consumer. The relative importance of these various spoilage processes may vary from product to product, with conditions of transportation and storage, with intended use etc., but the consequences of bacterial growth are commonly an important contributory factor. This is especially the case for chilled-fresh foods.

Determinations of the extent and/or precise nature of spoilage may be required for routine quality assurance, for regulatory purposes or for establishing the cause for any particular condition and hence appropriate remedial action. Sensory and microbiological criteria are traditionally used for these purposes, but both have their limitations. The subjectivity of sensory data poses many problems in routine use, not least because of the difficulties in assigning meaningful criteria for differentiating "acceptable from non-acceptable" (or "spoiled from non-spoiled") product. While total bacterial numbers often bear some relationship to acceptability, there are still problems in their use. Not all bacteria growing on food necessarily contribute to spoilage, nor is there a consistent relationship between bacterial numbers and spoilage. Thus, high pH meat (dark, firm, dry: DFD), spoils at lower cell densities than normal-pH meat under identical storage conditions whereas, on vacuum-packaged meat, bacterial numbers may reach a maximum and then remain unchanged for significant periods without obvious sensory change.

Measurement of chemical change, whether of microbial or non-microbial origin, offers a possible alternative to microbiological and sensory criteria. For example, an electrochemical method for glucose and enzyme sensors for nucleotide degradation products and for certain amines have already been proposed.

It has been found by Dainty et al., J. Appl. Bact., (1985), 59, 303–309 and J. Appl. Bact., (1989), 66, 281–289 that the volatile compound diacetyl (butane 2,3-dione) is produced during chill storage of red meats with free access to air (through a permeable film overwrap) or in high $O_2/CO_2$ gas atmospheres, and that diacetyl has a high potential as an index of freshness/acceptability/spoilage. This compound has been detected consistently during storage, and at relatively early stages when sensory changes were restricted to development of staleness rather than obvious spoilage. Evidence indicating that accumulation may also occur in vacuum packs has also been suggested as a measure of the condition of some citrus fruit juices and the sanitary status of the processes used in their manufacture, and as a means of detecting supplementation of aroma constituents to mask organoleptic defects in butter. Diacetyl has also been employed as an additive in the manufacture of margarine and cheese. Additionally it is produced during yeast fermentation and plays a role in the flavouring of beer. Sensitive, rapid methods for detection and analysis of diacetyl, which can be applied on- or at-line, to monitor food manufacturing processes and quality deterioration during transportation and storage, would therefore be of great value, as such methods would be non-destructive and would minimize the potential hygiene problems associated with the invasive sampling needed for analysis of non-volatile compounds. Such methods have not so far been available.

DESCRIPTION OF THE INVENTION

Accordingly, the present invention provides a method of monitoring the presence of diacetyl comprising exposing an aromatic ortho-diamine at acidic pH to an environment containing, or possibly containing, diacetyl and detecting any change in absorption or reflection of electromagnetic radiation due to the ortho-diamine. The change may suitably, though not necessarily, be in the UV or visible region or both.

The aromatic ortho-diamine preferably has the general formula (I)

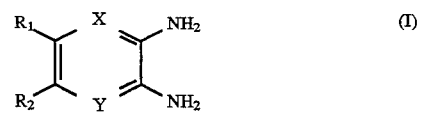

wherein each X and Y, which may be the same or different, represents —N— or —CH—, $R^1$ is a conjugated system which may be linear or cyclic or a combination thereof, $R^2$ is a conjugated system, which may be linear or cyclic or a combination thereof, or a hydrogen atom or a non-conjugated monovalent substituent group or $R^1$ and $R^2$ together form a cyclic or multicyclic conjugated system; or, when X and/or Y is —CH—, $R^1$ and X and/or $R^2$ and Y together form a cyclic or multicyclic conjugated system.

The diamine may initially be either neutral or in salt form and additionally and preferably, may then have been complexed with a transition metal such as nickel or cobalt. The groups $R^1$ and $R^2$, independently, or when part of a ring system including X or Y, may be substituted. $R^2$ may be a hydrogen atom or a simple monovalent substituent such as hydroxy or alkoxy. Preferably $R^2$ is hydrogen and $R^1$ is a phenyl or benzoyl group which may be substituted, especially by one or more amino groups.

Especially preferred o-diamines are 3,4-diaminobenzophenone and 3,3-diaminobenzidine, especially when complexed with a transition metal such as nickel or cobalt in the presence of an inorganic ligand such as chloride or perchlorate. A particularly preferred o-diamine is a complex of nickel chloride with 3,3'-diaminobenzidine which has been found to exhibit a colour change from pale mauve to brown/red, readily detectable with the naked eye.

The invention also includes the transition metal complexes of compounds of formula I, which are believed to be novel per se and have been found to have particular utility in the detection of diacetyl.

It will be appreciated that the selection of o-diamine will depend on the use to which the monitoring method is to be put, it being borne in mind that there is a need to protect the foodstuffs from direct contact or contamination with diamines which could be considered as toxic.

The diacetyl, when present, may be in liquid or gaseous phase, but, especially when the method is being used for food monitoring, it will conveniently be in gaseous phase released to the environment adjacent the foodstuff as a result of bacterial changes in the foodstuff. It has been found that, employing certain ortho-diamines as defined above, it is possible to detect visually concentrations of diacetyl in the region of 10 ppm.

The change in absorption or reflection of electromagnetic radiation due to the ortho-diamine may conveniently be a colour change detected visually, especially if only a qualitative monitor of the presence or absence of diacetyl is required. Alternatively, the change may be detected by any convenient spectroscopic method such as measurement of the transmittance and/or reflectance spectra, suitably employing fibre optics. The change may be detected by removing a sample of gas from the environment in which diacetyl may be present for detection, for example, spectroscopically. However, preferably, the monitoring is carried out in situ, for example by providing a suitable o-diamine doped substrate on the packaging or adjacent the foodstuff to be monitored, suitably by using a fibre light guide to and from the doped substrate to enable detection by remote measurement. Alternatively an optical fibre may be itself coated with the o-diamine and, if necessary, the coating sealed with a further coating layer of transparent or translucent, diacetyl-permeable, polymeric material. Such an optical fibre may, for example, be mounted within a storage refrigerator to enable detection in situ of a colour change resulting from spoilage of stored foodstuffs. It is envisaged therefore that optical fibres, or a network thereof, may be used in connection with commercial refrigeration plants, the fibres acting to allow monitoring of the transmission of thin film of suitably activated diamine, the reflectance of a thin film of suitably activated diamine or the transmission characteristics of a fibre cladded with a thin film of suitably activated diamine.

Therefore, according to a further aspect of the invention, there is provided an apparatus suitable for use in the monitoring method as described above comprising a source of electromagnetic radiation of wavelength covering the region in which the change is to be detected, means for transmitting such radiation to an aromatic ortho-diamine, means for exposing the ortho-diamine to the environment to be monitored and means for detecting a change in absorption or reflection of the electro-magnetic radiation due to the ortho-diamine.

The invention is intended to be applicable to such activities as monitoring the spoilage of chilled red meats with free access to air, or in high $O_2/CO_2$ atmospheres, in vacuum packs, for example in packs of certain citrus fruit products such as juices or in monitoring the spoilage or change in condition of products including butter substitutes and beer. The invention is also applicable to the monitoring of the "gaminess" of hung game, for example, with the aim of assessing the precise day on which the product has reached premium condition.

It will be appreciated that the monitoring method of the invention can be used to detect spoilage or change in food condition, during initial processing and packaging, during transportation, for example from one country to another in chilled containers, or during more local distribution to the retailer, as well as at the retail outlets themselves. A preferred method of carrying out the invention therefore comprises the incorporation of the aromatic ortho-diamine into the package or container for those foodstuffs which are known to generate diacetyl, so that any diacetyl generated can be monitored at one or more of the various stages of processing, packaging, transportation, distribution and retailing.

Therefore according to a further aspect of the invention, there is provided a foodstuff package, at least a portion of which incorporates an aromatic ortho-diamine, the diamine being positioned so as to be in contact with the environment surrounding the foodstuff.

The invention also provides a device intended for handling foodstuff known on spoilage or change in condition to generate diacetyl, at least a portion of which device incorporates an aromatic ortho-diamine, the diamine being positioned so that, in use, it will be in contact with the environment surrounding the foodstuff. The device can conveniently be a container for the transportation of such foodstuff, but may also be part of a processing or packaging line for the foodstuff. The term foodstuff is intended to include beverages such as fruit juice and beer.

The ortho-diamine may conveniently be applied to such a package or device in the form of a patch bearing the ortho-diamine, integral with the packaging or container, or subsequently applied thereto. Such a patch may be applied initially at the packaging station or at a late stage. It may be convenient to apply a series of such patches to monitor different stages in the progress of the foodstuff from source to retailer. Any acid component so as to give an acidic pH for the detection of diacetyl using the ortho-diamine can be provided at source or at a later stage when it is desired to effect monitoring. It will be appreciated that such a patch, while being in contact with the environment containing the foodstuff, need not contact the foodstuff itself, but can be in a semi permeable region of the package. The diamine may be protected by an exterior coating from external damage so long as the change in absorption or reflection can still occur and be detected. The use of patches as described above is particularly convenient when the ortho-diamine is capable of giving a visually-detectable colour change on exposure to diacetyl. When monitoring a visually-detectable change, by reflectance, the colour change can be enhanced by incorporating secondary colouring material into the activated diamine.

BRIEF DESCRIPTION OF THE DRAWINGS

The invention will now be further described with reference to the accompanying drawings in which.

EXAMPLES

Figure 1:
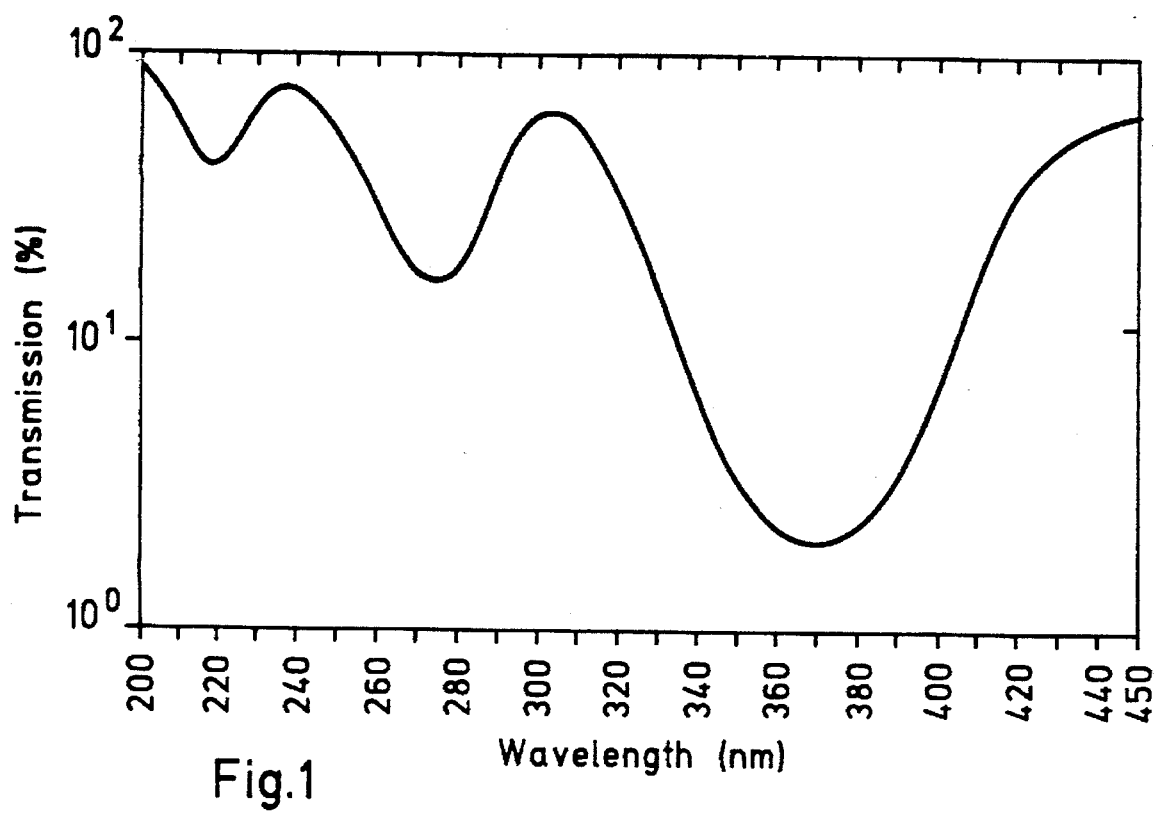
FIGS. 1–3 show transmission measurements of an exposed dye relative to an unexposed dye reference film for compounds III, IV and V, respectively.

Example 1 Preparation of o-Diamine/Transition Metal Complexes a) 3,3-diaminobenzidine/nickel dichloride complexes (II) and (III)

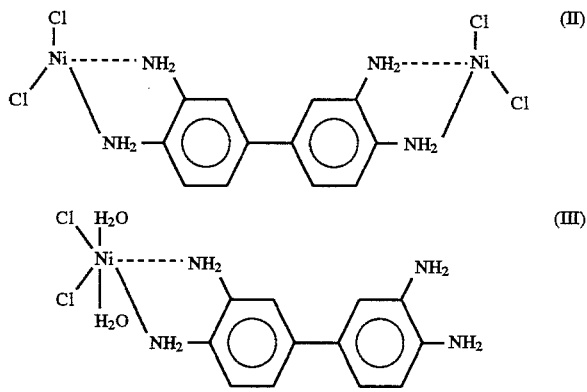

3,3'-diaminobenzidine (0.001M; 0.23 g) in ethanol (25 ml) was added dropwise under reflux to $NiCl_2.6H_2O$, (0.002M; 0.47g) in ethanol (5 ml). After 3 hours the reaction mixture was cooled in air, a pale dirty white precipitate was collected by vacuum filtration, which was washed with ethyl acetate, petroleum ether and water, then dried in an evacuated dessiccator over $P_2O_5$. The addition of water changed the complex's colour to pale mauve. Despite a 2:1 addition of $NiCl_2.6H_2O$ to diamine, the octahedral 1:1 complex (III) was always formed in the presence of water. In the absence of water a tetrahedral, 2 metals to 1 ligand, complex (II) was obtained. The reflux time was varied and longer times gave the same results as the product after 2–3 hours. Larger quantities in the same ratios yielded the same product.

b) 3,3'-diaminobenzidine/cobalt dichloride complex (IV)

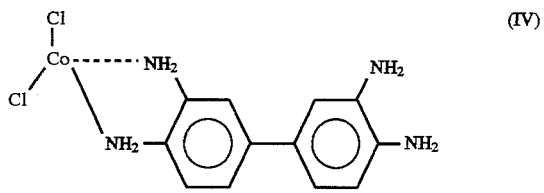

The reaction described in a) above was carried out except that $CoCl_2.6H_2O$ in ethanol was used instead of $NiCl_2$. On cooling, the precipitate was filtered under vacuum, washed with ethanol and dried in an evacuated dessicator over $P_2O_5$.

c) 3,3'-diaminobenzidine/nickel dichlorate complex (V)

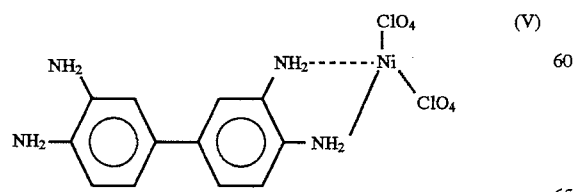

$Ni(ClO_4)_2.6H_2O$, (0.004M; 1.6 g), in ethanol was heated under reflux. 3,3'-diaminobenzidine was added (0.002M) dropwise in ethanol. This was refluxed for 5 hours. The pale grey product was washed with warm ethanol, then warm petroleum spirit (40–60° C.) and finally warm methyl acetate (approx. 50ml each).

The resulting solid was dried as described in a) above.

The above reaction was repeated but using chloroform instead of ethanol. The reaction mixture (using the same ratios of reactants as given above) was refluxed for 6 hours and then left to cool for 12 hours before refluxing for a further 8 hours. The resulting pale grey solid was collected by vacuum filtration, washed with chloroform and dried as described in a) above.

Example 2 Use of o-Diamines and Their Transition Metal Complexes for Detection of Diacetyl A dilute ethanolic solution of each of II, III, IV and V was prepared, together with similar solutions of 3,3'-diaminobenzidine and 3,4-diaminobenzophenone. Compound VI was made up in dimethylformamide.

One or two drops of concentrated hydrochloric acid were added for each approximately 50 ml of solution. A strip of Whatman filter paper was soaked in this solution and then air dried. The strip was now ready to be exposed to diacetyl. This was done in an enclosed flask containing a low concentration (minimum 10 ppm approx.) of diacetyl. All the dyes and complexed dyes reacted with diacetyl resulting in a colour change observeable with the naked eye. However, the attendant changes in the UV region were up to 100 times more intense than those in the visible region.

Examples of the colour changes which were obtained are as follows:

| Dye | Metal Salt | Colour Change |
|---|---|---|
| 3,3'-diaminobenzidine | nickel chloride hexahydrate (III) | grey → yellow/red |
| 3,3'-diaminobenzidine | cobalt chloride hexahydrate (IV) | blue → orange/yellow |
| 3,3'-diaminobenzidine | nickel chlorate hexahydrate (V) | pale purple → orange/yellow |
| 3,4'-diaminobenzophenone | nickel chloride hexahydrate | pale green → yellow |

Other dyes, when evaporated onto filter paper, were colourless, but on exposure to diacetyl vapour, developed a yellow colouration.

It was found that with compound (III) approximate diacetyl vapour concentrations as low as 0.6 ppm produced an observable colour change. Clearly, the use of intensity changes in the UV enable levels of diacetyl below 0.1 ppm to be detected.

Figure 2:
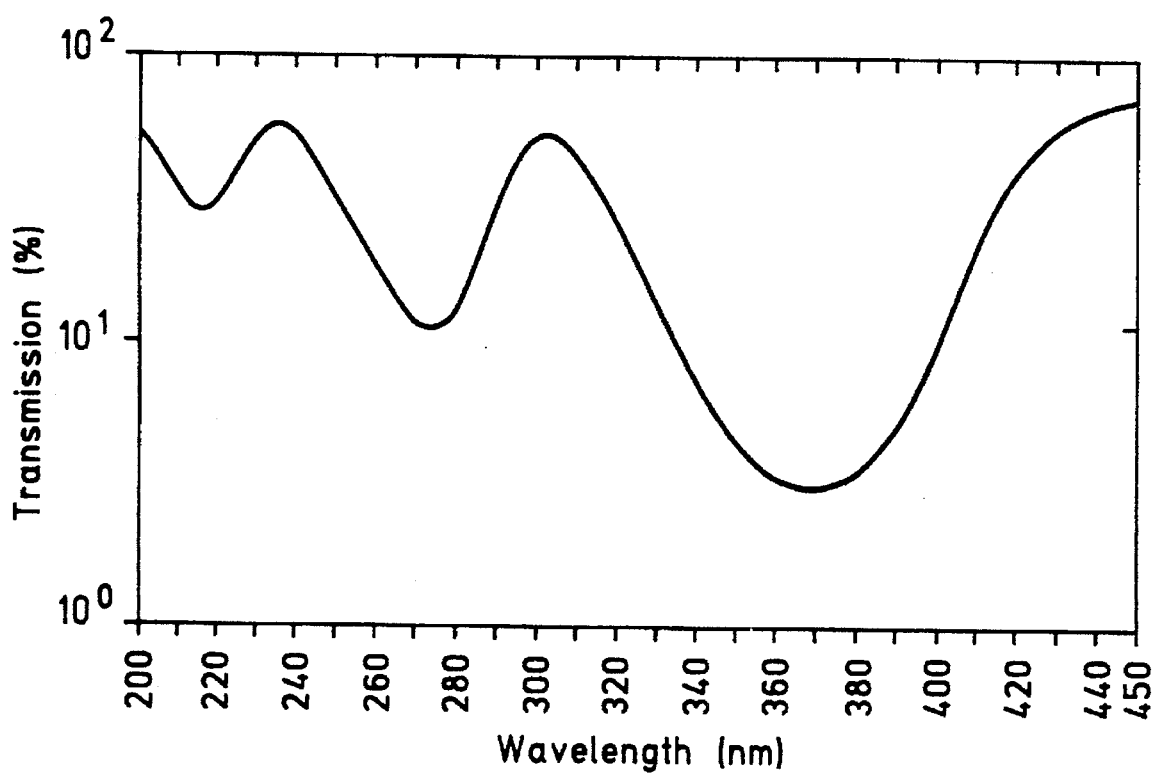
Figure 3:
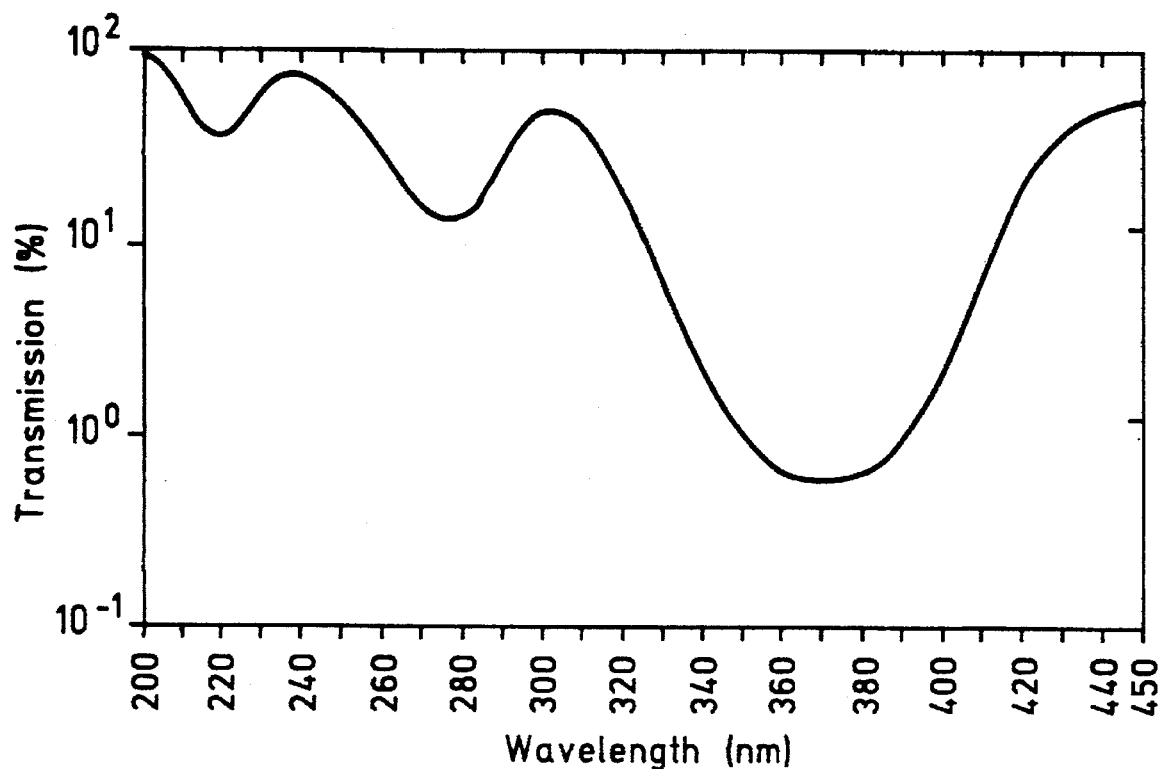

FIGS. 1, 2 and 3 show transmission measurements of the exposed dye (i.e. to diacetyl) relative to an unexposed dye reference film for compounds III, IV and V respectively. It will be appreciated that all spectroscopic features shown are solely due to reaction between the dye and the diacetyl.

Example 3 Use of o-Diamines in Detecting Diacetyl

A series of eight commercially available o-diamines were tested for their ability to detect diacetyl as follows:

Test-tube experiments were set up using microspatula quantities of the diamine and equal quantities of solvent, diacetyl and concentrated hydrochloric acid. The solvent used depended on the solubility of the diamine. Controls of diamine, acid and solvent as well as diacetyl, acid and solvent were also set up for comparison with the reaction test-tubes. The results obtained were as follows:

| Diamine | Solvent Colour without diacetyl | Colour with diacetyl |
| --- | --- | --- |
| 3,4-diaminobenzoic acid | pale orange | khaki green |
| 4-chloro-1,2-phenylene-diamine | pale pink | khaki green |
| 3,3'-diaminobenzidine | deep orange | dark brown |
| 3,4-diaminobenzophenone | pale orange | lime green |
| 2,3-diaminonaphthalene | pale golden | dark green |
| 4,5-dimethyl-1,2-phenylene-diamine | dark orange | dark brown & fawn precipitate |
| 1,2-phenylene diamine | pale pink | lime green |
| 2,3-diaminotoluene | deep orange | dark brown |

Most of these reactions were not immediate but happened over a period of time. The longer the solutions were left the more the colour developed.

The reaction conditions were investigated as follows:

Variable concentrations of acid from 2 molar to concentrated were used with quantities of diacetyl and diamine. The diamines used were those which had previously shown a positive colour reaction. It was found that the reaction would only proceed with concentrated acid, but only a quarter of the amount of acid to diacetyl/diamine was needed to implement the reaction.

Diamine concentration was effectively reduced to 0.002 molar concentration, dilution being with either ethanol or methyl sulphoxide.

Reactions were carried out at room temperature, but on heating the reaction proceeded more rapidly and on cooling in ice the reaction proceeded more slowly.

Various dilutions of diacetyl in the appropriate solvent were tested with the already established optimum conditions. Significant colour changes were still observed using 0.08% concentrations of diacetyl.

To investigate the use of diacetyl vapour, a simple experiment was set up using concentrated diacetyl and stoppered boiling tubes. Strips of filter paper were dipped into the appropriate diamine solutions and allowed to dry. They were then inserted into the bungs which were used to stopper boiling tubes containing small amounts of diacetyl. The tubes were left to stand to allow a build-up of diacetyl vapour within them and the filter papers compared with controls with no dried diamine on them. The colour changes on the filter papers compared favourably with those seen in solution.

Using optimum conditions already established 0.0001 molar concentration transition metal halides were introduced into the reaction mixtures. Colour changes were very strong for those solutions in which the reaction was already pronounced. The colour changes were cobalt (blue to green), magnesium (green to yellow), iron (green to colourless).

Example 4 Use of Fibre Optics in Detecting Diacetyl

Figure 4:
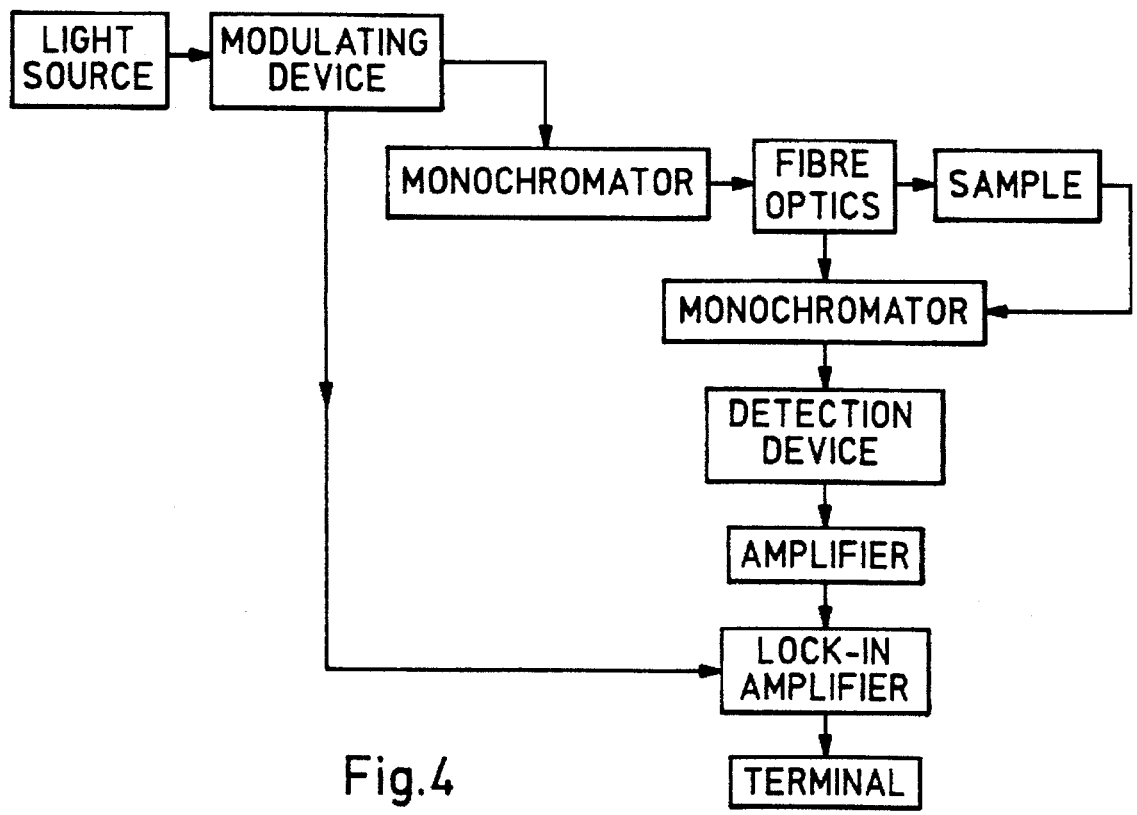
FIG. 4 shows schematically a flow rig useful for detecting diacetyl.

Diacetyl is detected using a flow rig as shown schematically in FIG. 4. The rig comprises a light source covering the spectral range of interest. For the compounds described above which exhibit colour change, this will be the visible region. Preferably, the range is versatile so that the most intense spectral change for each dye used can be investigated with the same light source.

The modulating device is a mechanical device which chops the incoming light at a particular frequency, while the monochromator, with a stepper motor, allows scanning of a spectral range so that the peak wavelength at which a change in colour is most intense for a particular dye is found. The fibre optics comprises a fibre bundle which uses the fibres as a light guide to and from the sample, i.e. a suitable base material coated with a dye as described above. The sample can be positioned at a site remote from the light source and detection equipment, which site is in contact with, or can be brought into contact with, the environment being monitored for diacetyl content. Such an environment will for example include the foodstuff or beverage which may be of unacceptable freshness. It will be appreciated that the light source and other equipment can therefore be protected from the potentially cold damp atmosphere where the foodstuff or beverage is being stored, e.g. a refrigerator.

The detection device is a photodiode which produces a readable current from the intensity of the incoming light while the amplifier amplifies the current output from the photodiode and converts the reading to a voltage output. The lock-in amplifier is directly connected to the mechanical chopper and locks in to that frequency, which means that only light which is at the chopper's frequency is read, so that ambient light is excluded. The analogue reading passes to the computer terminal which can perform operations such as recording, storing and manipulation of the measurements.

It will be appreciated that the detection means and energising means can be varied to suit the particular application.

I claim:

1. A method of determining the presence of diacetyl in a gaseous environment comprising:
   exposing to said gaseous environment an aromatic ortho-diamine transition metal complex at acid pH;
   detecting any change in absorption or reflection of electro-magnetic radiation by the ortho-diamine, and determining the presence of said diacetyl from said detected change.

2. A method according to claim 1, wherein the diacetyl is in a vapor state.

3. A method according to claim 1, wherein the gaseous environment includes the vapor state.

4. A method according to claim 1, wherein the aromatic ortho-diamine has the general formula (I)

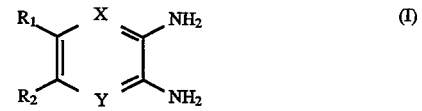

wherein X and Y are the same or different and represent —N—, —C— or —CH—, $R^1$ is a conjugated system which may be linear or cyclic or a combination thereof, $R^2$ is a conjugated system, which may be linear or cyclic or a combination thereof, or a hydrogen atom or a non-conjugated monovalent substituent group or $R^1$ and $R^2$ together form a cyclic or multicyclic conjugated system; provided that when X or Y are —C—, $R^1$ and X or $R^2$ and Y together form a cyclic or multicyclic conjugated system.

5. A method according to claim 1, wherein $R^2$ is hydrogen and $R^1$ is a phenyl or benzoyl group.

6. A method according to claim 1, wherein the ortho-diamine is 3,4-diaminobenzophenone.

7. A method according to claim 1, wherein the ortho-diamine is 3,3'-diaminobenzidine.

8. A method according to claim 1, wherein the ortho-diamine is absorbed onto a substrate which is positioned to be in contact with the environment surrounding the foodstuff.

9. A method according to claim 1, wherein use is made of fiber optics in the detection of a change in absorption or reflection of electromagnetic radiation by the ortho-diamine.

10. A method according to claim 1, wherein $R^2$ is hydrogen and $R^1$ is a phenyl or benzoyl group substituted by one or more amino groups.

11. A method according to claim 10, wherein the ortho-diamine is a complex of nickel chloride with 3,3'-diaminobenzidine.

12. A non-invasive method of determining the presence of diacetyl in a foodstuff surrounding gaseous environment comprising the steps of:

contacting a substrate impregnated or doped with an ortho-diamine transition metal complex at acidic pH with the gaseous environment surrounding the foodstuff;

detecting any change in the absorption or reflection of electro-magnetic radiation by the ortho-diamine, and determining the presence of said diacetyl from said detected change.

13. A non-invasive method of determining the extent of food spoilage associated with the foodstuff wherein a gaseous environment surrounds the foodstuff comprising the steps of:

contacting a substrate impregnated or doped with an ortho-diamine transition metal complex at acidic pH with the gaseous environment surrounding the foodstuff;

detecting any change in the absorption or reflection of electro-magnetic radiation by the ortho-diamine; assessing the extent of said change;

determining therefrom the extent of food spoilage associated with said foodstuff.

\* \* \* \* \*